United States Patent [19]

Baumann et al.

[11] 4,323,781

[45] Apr. 6, 1982

[54] TOMOGRAPHIC X-RAY DIAGNOSTIC UNIT WITH THE SECONDARY OF THE HIGH VOLTAGE TRANSFORMER ROTATING WITH THE X-RAY SOURCE

[75] Inventors: Heinz Baumann; Werner Kuehnel, both of Uttenreuth; Manfred Rattner, Buckenhof, all of Fed. Rep. of Germany

[73] Assignee: Siemens Aktiengesellschaft, Berlin & Munich, Fed. Rep. of Germany

[21] Appl. No.: 94,766

[22] Filed: Nov. 16, 1979

[30] Foreign Application Priority Data

Dec. 21, 1978 [DE] Fed. Rep. of Germany ....... 2855379

[51] Int. Cl.³ ............................................. G21K 5/10
[52] U.S. Cl. ................................. 250/422; 250/445 T; 336/120; 336/122
[58] Field of Search .................... 250/445 T, 421, 422; 336/120, 122

[56] References Cited

U.S. PATENT DOCUMENTS

| | | | |
|---|---|---|---|
| 3,611,230 | 10/1971 | Maake | 336/120 |
| 3,924,174 | 12/1975 | Fahrner | 336/120 |
| 4,051,378 | 9/1977 | Krippner | 250/421 |
| 4,093,859 | 6/1978 | Davis et al. | 250/445 T |

*Primary Examiner*—Davis L. Willis
*Attorney, Agent, or Firm*—Hill, Van Santen, Steadman, Chiara & Simpson

[57] ABSTRACT

In an exemplary arrangement a rotatable scanning system comprises an X-ray tube which emits a beam of X-rays which penetrates the layer to be examined, and a radiation receiver which supplies electrical output signals corresponding to the measured radiation intensity. A computer is connected to the radiation receiver for calculating the attenuation values of specific image points of the irradiated body layer from the output signals of the radiation receiver. An inductive transformer is provided for transmitting energy to the X-ray tube, its secondary winding being arranged in a fixed position relative to the X-ray tube and rotating with the scanning system and its primary winding being fixed relative to the stationary part of the unit.

6 Claims, 8 Drawing Figures

TOMOGRAPHIC X-RAY DIAGNOSTIC UNIT WITH THE SECONDARY OF THE HIGH VOLTAGE TRANSFORMER ROTATING WITH THE X-RAY SOURCE

BACKGROUND OF THE INVENTION

The invention relates to an X-ray diagnostic unit for producing layer images of a radiography subject with a patient support, with a rotatable scanning system for irradiating the radiography subject from various directions comprising an X-ray tube which emits a beam of X-rays which penetrates the layer to be examined and whose dimension perpendicular to the layer plane is equal to the layer thickness, and a radiation receiver which supplies electrical output signals corresponding to the measured radiation intensity, with an X-ray generator for supplying the X-ray tube and with a computer connected to the radiation receiver for calculating the attenuation values of specific image points of the irradiated body layer from the output signals of the radiation receiver.

With a computer-tomograph of this type, the time of examination is determined essentially by the scanning time of the scanning system. The known method is to rotate the scanning system by an angle of approximately 360° about the patient for one scan and then move it back again into its starting position for the next scan. In this case, the X-ray tube may be connected via high voltage cable to the X-ray generator and the detector may be connected via cable to the electronic device processing the measured values. The times required for accelerating the scanning system, however, determine lower limits for the scanning time. It would be possible to shorten the scanning time if the scanning system could be moved more quickly, more particularly if it were continuously rotating. In this case cables for supplying current or conducting away signals could no longer be used for the X-ray tube or for the radiation receiver.

SUMMARY OF THE INVENTION

The underlying object of the invention is to design a unit of the type initially mentioned, so that no high voltage cables are required between the stationary and rotating components in order to supply high voltage to the X-ray tube.

According to the invention, this object is achieved by providing an inductive transformer for transmitting energy to the X-ray tube, the secondary winding of this transformer being arranged in a fixed position relative to the X-ray tube and rotating with the scanning system and the primary winding being in a fixed position in the stationary part of the unit. In a diagnostic radiology unit according to the invention, the energy is transmitted to the X-ray tube by inductive coupling and thus in a contact-free manner. It is therefore possible to let the scanning system rotate continuously and to carry out a scan in a very short time, on the order of magnitude of 0.1 second. The possibility of also examining moving organs is thereby created.

An advantageous development of the invention resides in the construction of the primary and secondary windings in the form of coaxial rings which enclose an opening for receiving the examination subject. In this case, the examination subject is moved into the transformer, the diameter of which has to be selected so that this action is possible. It is also possible to construct the primary winding as a tube arranged in a fixed position in the unit and enclosed by the core which is arranged in a fixed position relative to the X-ray tube and rotates with the scanning system and to wind the secondary winding on to the core. In this case the examination subject is introduced into the tube forming the primary winding.

The invention is explained in more detail in the following with reference to several exemplary embodiments represented on the accompanying sheets of drawings; and other objects, features and advantages will be apparent from this detailed disclosure and from the appended claims.

DETAILED DESCRIPTION

Figure 1:
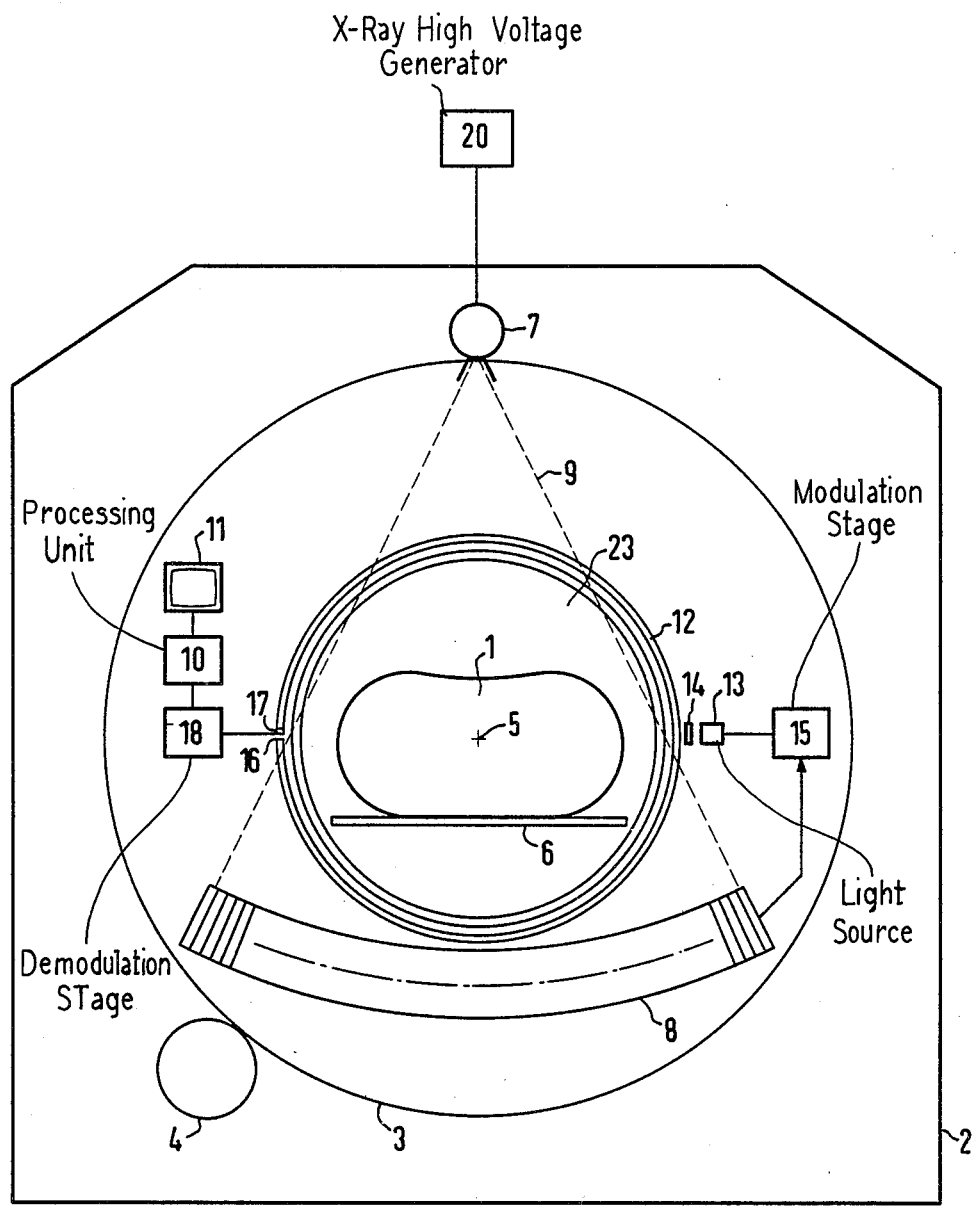
FIG. 1 shows an X-ray diagnostic unit to illustrate the idea behind the invention.

FIG. 1 represents an X-ray diagnostic unit, a so-called computer tomograph, for producing transverse layer images of a patient 1. In a housing 2 the unit has a rotating frame 3 which is rotatable by means of a motor 4 about an axis 5 running perpendicularly to the drawing plane. An X-ray tube 7 and a detector 8 for x-radiation are provided for scanning the patient 1 lying on a patient support 6. The X-ray tube 7 emits a fan-shaped beam of X-rays as indicated at 9, the extent of which is selected so that the entire transverse layer of the patient 1 to be examined is penetrated by x-radiation. Perpendicularly to the layer plane, the thickness of the beam of X-rays 9 is equal to the layer thickness; namely, a few millimeters.

In order to scan the patient 1, the scanning system here comprising X-ray tube 7 and the detector 8 as well is turned about the patient 1 by an angle of approximately 360° and, at predetermined projections, for example at each degree of angle, a set of output signals of the detector 8 is read. The detector 8 comprises a row of individual detectors, e.g. 256 individual detectors, so that, for example, 256 signals of the radiation receiver 8 are read for each projection and for example 360×256 signals are available for processing for each scanning operation. In a manner described in more detail in the following the signals are transmitted to a stationary data processing unit 10 which calculates from them the attenuation values of prescribed points in the examined transverse layer of the patient 1 in the form of a matrix and reproduces this as an image on a monitor 11.

In the exemplary arrangement, where the detector is also rotated, a stationary ring 12 which is curved around the rotating axis 5 and which consists of a light-conducting material, e.g. synthetic glass, is provided for transmitting the detector signals, a light source 13 beaming onto its surface via an optical system 14. The light source 13 is connected to a modulation stage 15 which converts the detector signals into light signals. A pulse space coding, for example, may be used for this purpose. The ring 12 is designed so that the light from the light source 13 is passed on over its entire periphery. It has a gap 16, and a light receiver 17, which converts the light signals back into electrical signals, is arranged at one of the boundary faces of the gap 16. These signals are demodulated in a demodulation stage 18 and supplied to the data processing unit 10. The signal transmission takes place successively during a projection, i.e. the detector signals of the individual detectors are transmitted successively by the described apparatus. The light source 13 may be, for example, a luminescence diode or laser diode operating in the infrared range. During a scan of the patient 1, the modulation stage 15, the light source 13 and the optics 14 rotate with the scanning system 7, 8, while the structural elements 12, 17, 18, 10, 11 remain stationary. A noncontact signal transmission therefore takes place from a rotating component to a stationary component. If the high voltage is transmitted to the X-ray tube 7 by an X-ray high voltage generator 20 in a noncontact manner, it is possible to allow the scanning system 7, 8 to rotate continuously and to obtain very short scanning times. A very high rotational speed may be selected for the rotating part, namely the rotating frame 3 with the scanning system 7, 8. The scanning of a radiography subject is effected in this connection during a predetermined angle of rotation of approximately 360° as the scanning system 7, 8 rotates at a constant rate with a time period per revolution corresponding to the desired tomographic scan time.

Figure 2:
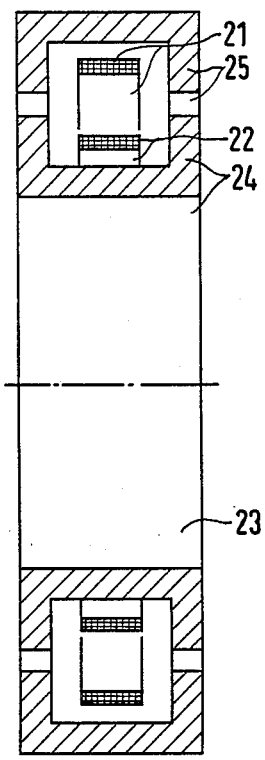
FIG. 2 shows an embodiment according to the invention of a transformer in the case of the X-ray diagnostic unit according to FIG. 1.

FIG. 2 shows an exemplary embodiment for carrying out contact-free, inductive energy transmission to the X-ray tube 7. In this exemplary embodiment the primary winding 21 and the secondary winding 22 of a transformer are designed as concentric rings which enclose the opening 23 serving to receive the patient 1. The transformer core is constructed as a shell-type core, enclosing the windings 21, 22, which core consists of two parts 24, 25 of U-shaped cross-section with flange-type side legs aligned in opposition. The core port 24 and the secondary winding 22 are arranged in a fixed position relative to the rotating frame 3 and thus to the X-ray tube 7 and rotate with the scanning system 7, 8. The other core part 25 and the primary winding 21 are provided in a fixed position in the stationary part of the unit. An annular air gap is left free between the two core parts 24, 25 so that relatively rotation is freely accommodated.

Figure 3:
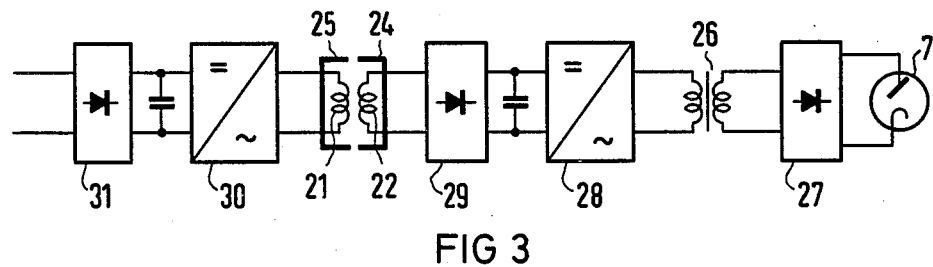
FIGS. 3 and 4 show circuit arrangements for illustrating the X-ray diagnostic unit according to FIGS. 1 and 2.

FIG. 3 shows that the X-ray tube 7 is supplied by a high voltage transformer 26 via a high voltage rectifier 27. The primary winding of the high voltage transformer 26 is connected to an inverter 28 for medium frequency in the order of magnitude of one to five kilohertz (1 to 5 kHz), the inverter being fed by a rectifier 29. The input of the rectifier 29 is connected to the secondary winding 22 of the transformer represented in FIG. 2. The primary winding 21 is fed by an inverter 30 for medium frequency which is connected to the power supply via a mains rectifier 31.

In the case of the arrangement according to FIG. 3, parts 7, 22 and 26 to 29 are arranged on the rotating frame 3, i.e. they rotate during the scan, while parts 21, 30, 31 are stationary. Part 24 of the core also rotates, while part 25 is stationary.

Figure 4:
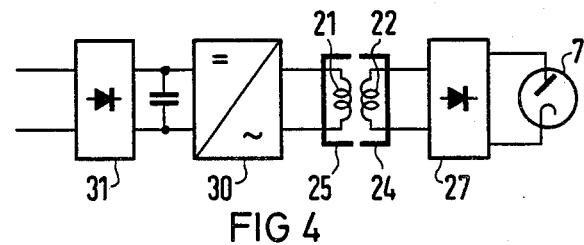

FIG. 4 represents a circuit arrangement in which the transformer 21, 22, 24, 25 itself forms the high voltage transformer. Its primary winding 21 is fed, as in the case of the example according to FIG. 3, by the inverter 30 which is connected via the mains rectifier 31 to the mains supply.

Figure 5:
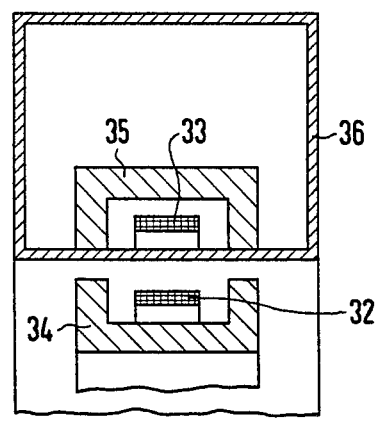
FIGS. 5 to 8 show three variants of the transformer for the X-ray diagnostic unit according to FIG. 1.

The transformer represented in FIG. 5 has a primary winding 32 and a secondary winding 33. Here too the windings 32, 33 are constructed as concentric rings which enclose an opening for receiving the patient 1. The transformer core is also constructed as a shell-like core enclosing the windings 32, 33 and consisting of two parts 34, 35 of U-shaped cross-section which, with their flange-type side legs are aligned in opposition. The core part 35 is arranged in a fixed position relative to the X-ray tube 7, i.e. it rotates with the scanning system 7, 8. The other core part 34 is provided together with the primary winding 32 in a fixed position in the unit. An air gap is also left here between the two core parts 34, 35. The secondary winding 33 and the core part 35 are arranged in a closed, hollow ring-shaped housing 36 which can also receive additional high voltage components, e.g. rectifiers, capacitors and possibly even the X-ray tube. For insulation purposes it may be filled with oil and rotates with the scanning system 7, 8, i.e. it is arranged in a fixed position on the rotating frame 3.

Figure 6:
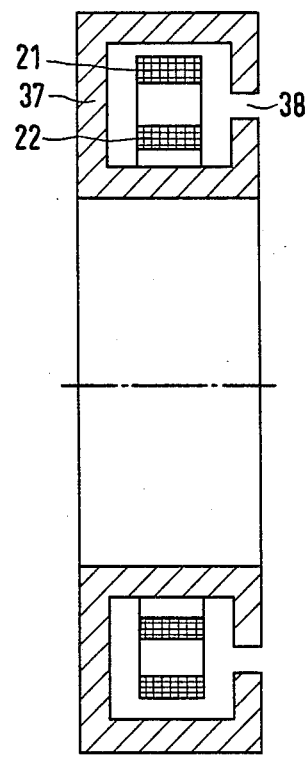

The transformer represented in FIG. 6 has, like the transformer according to FIG. 2, a primary winding 21 and a secondary winding 22 which are placed concentrically to one another. The core, however, is constructed as a hollow ring 37, mounted in a fixed position in the housing, and the windings 21, 22 are disposed inside it. The core 37, in which the winding 22 rotates while the winding 21 remains stationary, is provided at its periphery with an air-gap 38, through which both the supply lines to the windings 21, 22 and the support mounting means for these windings may be passed.

Figure 7:
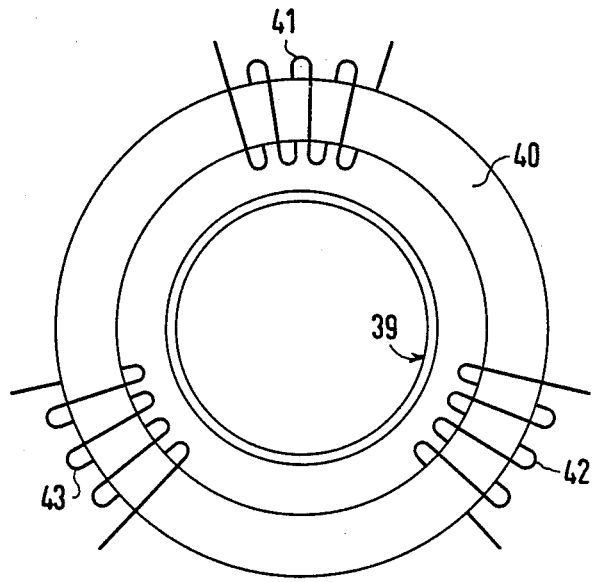
Figure 8:
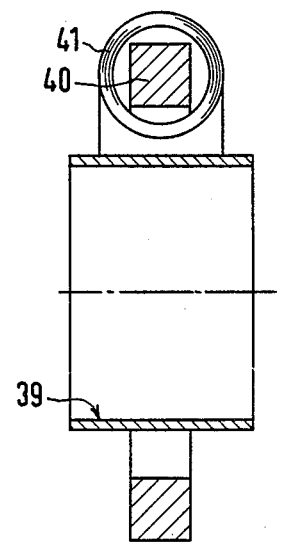

In the case of the transformer represented in a front view in FIG. 7 and in a section in FIG. 8, the primary winding is constructed as a tube 39 which is arranged in a fixed position in the unit and which is enclosed by the core 40 arranged in a fixed position relative to the X-ray tube 7, i.e. fixed on the rotating frame 3 and thus rotating with the scanning system 7, 8. Three secondary windings 41, 42, 43 are wound on the core 40. The secondary winding is thus formed, in the case of the example according to FIG. 7, by three component windings.

It is known in the art to use a measurement arrangement with a rotary X-ray source and a stationary detector array extending for 360° about the axis of rotation of the X-ray source, in which case the coupling of detector signals between a rotary detector and a stationary processing and display system is not required.

The use of an arcuate light guide such as 12 for coupling with modulated light signals being transmitted from a continuously rotating X-ray detector such as 8 is disclosed in greater detail in German application P 28 46 526.1 filed Oct. 25, 1978 (which is expected to be published in about April 1980), and which corresponds with a U.S. application for patent Ser. No. 078,052 filed Sept. 24, 1979, assigned to the assignee of the present application (and bearing the assignee designation VPA 78 P 5114).

It is true for all the exemplary transformers according to FIGS. 2, 5, 6, 7 that the transformer represented here may be an intermediate transformer connected before the high voltage transformer according to FIG. 3, but that it may also form the high voltage transformer itself according to FIG. 4.

It will be apparent that many modifications and variations may be effected without departing from the scope of the novel concepts and teachings of the present invention.

We claim as our invention:

1. An X-ray diagnostic unit for producing layer images of a radiography subject, comprising a patient support, a rotatable scanning system for irradiating the radiography subject from various directions having an X-ray tube, which emits a beam of X-rays penetrating the layer to be examined and whose dimension perpendicular to the layer plane is equal to the layer thickness, a radiation receiver which supplies electrical output signals corresponding to the measured radiation intensity, an X-ray high voltage generator for supplying the X-ray tube and a processing unit connected to the radiation receiver for calculating the attenuation values of specific image points of the irradiated body layer from the output signals of the radiation receiver, characterized in that, an inductive coupling means (FIGS. 2, 5, 6, 7, 8) is provided for transmitting energy to the X-ray tube (7), having a secondary winding (22, 33, 41, 42, 43) arranged in a fixed position relative to the X-ray tube (7) and rotating with the scanning system (7, 8) and having a primary winding (21, 32, 39) stationary in the unit, characterized in that the primary winding (21, 32) and the secondary winding (22, 33) are constructed as concentric rings which enclose an opening (23) for receiving the radiography subject (1).

2. A unit according to claim 1, characterized in that the coupling means comprises a transformer core (24, 25, 34, 35) constructed as a shell-type core enclosing the windings (21, 22, 32, 33), said core comprising two parts of U-shaped cross section with flange-type side legs aligned in opposition, in that one half of the core (24, 35) is arranged in a fixed position relative to the X-ray tube (7) and rotates with the scanning system (7, 8), in that the other half of the core (25, 34) is in a fixed position in the unit and in that an air gap is left between the two halves of the core (24, 25, 34, 35).

3. A unit according to claim 2, characterized in that the secondary winding (33) and the rotating half of the core (35) together with additional high voltage components are arranged in a closed, hollow ring-shaped housing (36).

4. A unit according to claim 1, characterized in that the core is constructed as a hollow ring (37) arranged in a fixed position in the unit, the primary winding (21) and the secondary winding (22) being located inside said hollow ring and in that on its periphery the core (37) has an opening (38) through which lines for conducting electrical energy may pass.

5. A unit according to claim 1, characterized in that the coupling means (FIGS. 2, 5, 6, 7, 8) is an intermediate transformer (FIG. 3), and that a high voltage transformer (26) is connected with the secondary winding of the coupling means.

6. A unit according to claim 1, characterized in that the coupling means (FIGS. 2, 5, 6, 7, 8) is a high voltage transformer (FIG. 4) having its secondary winding connected with the X-ray tube via a transformer-free conductive path.

* * * * *